United States Patent [19]
Cho et al.

[11] Patent Number: 6,068,846
[45] Date of Patent: May 30, 2000

[54] METHODS AND MATERIALS FOR TREATING DEPRESSION AND MOOD DISORDER

[75] Inventors: Suk H. Cho, Idaho Falls; Lynn Perkes, Rexburg, both of Id.

[73] Assignee: Melaleuca, Incorporated, Idaho Falls, Id.

[21] Appl. No.: 09/368,789

[22] Filed: Aug. 5, 1999

Related U.S. Application Data

[60] Provisional application No. 60/095,378, Aug. 5, 1998.

[51] Int. Cl.⁷ .......................... A61K 35/78; A61K 31/70; A61K 31/495; A61K 31/35; A61K 31/34
[52] U.S. Cl. .................. 424/195.1; 514/52; 514/252; 514/451; 514/474
[58] Field of Search .................. 424/195.1; 514/252, 514/451, 52, 474

[56] References Cited

U.S. PATENT DOCUMENTS

| | | | |
|---|---|---|---|
| 4,472,387 | 9/1984 | Laruelle et al. | 424/180 |
| 5,820,867 | 10/1998 | Bewicke | 424/195.1 |
| 5,911,992 | 6/1999 | Braswell et al. | 424/195.1 |

*Primary Examiner*—Raymond Henley, III
*Attorney, Agent, or Firm*—Fish & Richardson P.C., P.A.

[57] ABSTRACT

The present invention provides methods and materials for the treatment of depression or mood disorder. Specifically, the invention involves the use of 5-HTP and an extract to treat depression or mood disorders when administered orally. In addition, the invention provides less expensive, naturally derived dietary supplements to treat mild to moderate depression or mood disorder.

30 Claims, No Drawings

METHODS AND MATERIALS FOR TREATING DEPRESSION AND MOOD DISORDER

RELATED APPLICATION

This application claims priority from U.S. Provisional Application Ser. No. 60/095,378, filed Aug. 5, 1998.

BACKGROUND

1. Technical Field

The present invention relates to methods and materials for the treatment of depression or mood disorder. More particularly, the invention relates to the treatment of mild to moderate depression or mood disorder by a novel composition of *Hypericum perforalum, Griffonia Simplicifolia*, and/or specific vitamins. The present invention relates to tablets, capsules, tinctures, or syrup containing a specific amount of *Hypericum perforalum, Griffonia Simplicifolia*, and/or specific vitamins for internal use.

2. Background Information

Depression is the most common mood disorder in the modern world. There are a variety of types and levels of depression. The spectrum of depression can range from a condition that is temporary, lasting a few days, to clinical depression that can be a much more serious disorder. This medical disorder can be characterized by persistent severe feelings of worthlessness, guilt, sadness, helplessness, and hopelessness. Common symptoms can include inactivity, difficulty thinking or concentrating, appetite changes, sleep disturbances, and suicidal tendencies. There are several theories that postulate why depression exists. Stressful life style, diet, chemical imbalances, and traumatic events are all thought to cause depression. Although the mechanisms of depression are not completely understood, therapies are available to treat this disorder. Treatments typically involve using antidepressant drugs in combination with counseling.

Approximately seventeen million Americans suffer from clinical depression and over twenty-eight million Americans take antidepressant drugs. Modern drugs focus on manipulating neurotransmitter levels in the brain. The most commonly used drugs are Prozac, Zoloft, and Paxil, which predominately work by increasing serotonin levels either by inhibiting the reuptake of serotonin or preventing serotonin breakdown. Most prescriptions can be expensive and patients can experience unwanted side effects from these medications. In addition, some of these medications can become ineffective after prolonged use.

SUMMARY

The present invention provides methods and materials for the treatment of depression or mood disorder. Specifically, the invention features compositions that can effectively treat depression or mood disorder when administered orally. In addition, the invention features less expensive, naturally derived dietary supplements to treat mild to moderate depression or mood disorder.

In general, the invention features a composition containing *Hypericum perforatum* extract and 5-HTP. The composition can contain a vitamin (e.g., thiamine, riboflavin, niacin, folic acid, vitamin C, pantothenic acid, vitamin $B_6$, and/or vitamin $B_{12}$). The vitamin can be from about 0.01 percent to about 90 percent of the composition. The vitamin can be naturally or synthetically derived. The *Hypericum perforatum* extract can be a dry extract or a concentrated extract of *Hypericum perforatum* flower tops or leaves. The *Hypericum perforatum* extract can be up to about 90 percent of the composition. The 5-HTP can be up to about 90 percent of the composition. The composition can be in the form of a tablet, encapsulate, or syrup. For example, the composition can be in the form of a tablet, and can contain a filler, binder, excipient, and/or coating. Alternatively, the composition can be in the form of an encapsulate, and can contain a filler; or the composition can be in the form of a syrup, and can contain a liquid carrier, preservative, and/or flavoring. The liquid carrier can be ethanol, water, and/or glycerine. The composition can contain hypericin where the hypericin is from about 0.001 percent to about 5.0 percent of the composition. The composition can contain quercetin where the quercetin is from about 0.001 percent to about 5.0 percent of the composition. The composition can contain pseudohypericin where the pseudohypericin is from about 0.001 percent to about 5.0 percent of the composition. The composition can contain rutin where the rutin is from about 0.001 percent to about 5.0 percent of the composition. The composition can contain hyperoside where the hyperoside is from about 0.001 percent to about 10 percent of the composition. The composition can contain isoquercetin where the isoquercetin is from about 0.001 percent to about 10 percent of the composition. The composition can contain a hydrophilic phytochemical. The composition can contain a mineral (e.g., calcium, magnesium, and chromium). The mineral can be up to about 25 percent of the composition. The composition can contain a lipophilic component of a phytochemical. The 5-HTP can be an extract from *Griffonia simplicifolia, Mucana pruriens* of legume, *Musa sapientum, Gossypium hirsutum*, and/or *Urtica dioica*. The 5-HTP can be more than about 0.01 percent of the composition. The 5-HTP can contain optically pure L-configuration 5-HTP. The composition can contain a *Ginko biloba* extract and/or a *Piper methysticum* extract.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Treatment of depression or mood disorder depends largely on a few central elements. Because mental and mood disorders are complex, with various mechanisms affecting them (e.g., serotonin reuptake inhibitors SSRI, monoaminooxidase (MAO) inhibitors), it is very difficult to treat the mental or mood disorder with one therapy. In addition, deficiency of any number of nutrients is quite common in depressed individuals. Further, lack of certain nutrients can effect mood and mental disorders. Since there is no panacea for treating mood or mental disorder and because prescription drugs have side effects, it is an objective of this invention to formulate a mild and safe product for consumers to improve mood disorder or depression.

The present invention features compositions containing 5-HTP (5-hydroxytryptophan) and St. John's Wort. In addition, these compositions can contain vitamins along with St. John's Wort and/or 5-HTP to improve mood or mental disorder.

The compositions of the invention can contain a combination of particular levels of St. John's Wort with hypericin and certain flavonoid markers, 5-HTP (or a plant that contains 5-HTP), and particular vitamins. For example, a composition of the invention can contain 0.01% to 90% w/w of dry extract weight or concentrated extract of flower top or leaves of St. John's Wort. Typically, 5–500 mg daily of dry weight or concentrated extract of St. John's wort formulated as tablets, syrups, or encapsulates can be used. In addition, the dry extract of St. John's wort can contain 0.001–5% of hypericin, 0.001–5% quercetin, 0.001–5.0% of pseudohypericin, 0.001–5.0% of rutin, 0.001–10% of hyperoside, and 0.001–10% of isoquercetin. The dry extract can also contain hydrophilic phytochemicals and minerals as well as lipophilic components of phytochemicals.

Further, a composition can contain 0.01–90% w/w of 5-HTP. The 5-HTP can be derived from the extraction of *Griffonia simplicifolia, Mucana pruriens* of legume, *Musa sapientum, Gossypium hirsutum* or *Urtica dioica*. The 5-HTP can be in these extracts or dry extracts at a level between 0.01–100%. In addition, the 5-HTP can be optically pure with L-configuration.

A composition within the scope of the invention also contains one or more vitamins. For example, thiamine can be at a level of between 0.0–25%, riboflavin at 0–25%, niacin at 0–25%, folic acid at 0–50%, vitamin C at 0–25%, pantothenic acid at 0–25%, vitamin $B_6$ at 0–25%, and/or vitamin $B_{12}$ at 0–25%. Vitamins can be natural or synthetically derived. The composition can also contain minerals such as calcium, magnesium, and chromium at any level such as 0–25%.

A composition can also contain the extract of Ginko biloba and/or *Piper methysticum*.

The invention will be further described in the following examples, which do not limit the scope of the invention described in the claims.

EXAMPLES

Example 1

Composition Containing *Hypericum perforatum* Extract

| Ingredient | Form | Wt % |
|---|---|---|
| Hypericum perforatum | Dry extract of flower tops with 0.3% hypericin | 62 |
| Griffonia Simplicifolia | White powder, 99.5% of 5-HTP | 5 |
| Folic Acid | 100% USP | 28 |
| Vitamin $B_{12}$ | Cyanocobalamin, 100% USP | 5 |

The ingredients are blended in a homogeneous mixer, and are encapsulated to provide the appropriate daily recommendation.

Example 2

Composition Containing *Hypericum perforatum* Extract

| Ingredient | Form | Wt % |
|---|---|---|
| Hypericum perforatum | Dry extract of flower tops with 0.3% hypericin | 62 |
| Griffonia Simplicifolia | White powder, 99.5% of 5-HTP | 10 |
| Folic Acid | 100% USP | 28 |

The ingredients are blended in a homogeneous mixer, and are encapsulated to provide the appropriate daily recommendation.

Example 3

Composition Containing *Hypericum perforatum* Extract

| Ingredient | Form | Wt % |
|---|---|---|
| Hypericum perforatum | Dry extract of flower tops with 0.3% hypericin | 70 |
| Folic Acid | 100% USP | 20 |
| Vitamin $B_{12}$ | Cyanocobalamin, 100% USP | 10 |

The ingredients are blended with cellulose, gelatin, and magnesium stearate. The blended materials are formed into tablets, and are coated with a food glaze to provide the appropriate daily recommendation.

Example 4

Composition Containing *Hypericum perforatum* Extract

| Ingredient | Form | Wt % |
|---|---|---|
| Hypericum perforatum | Dry extract of flower tops with 0.3% hypericin | 62 |
| Griffonia Simplicifolia | White powder, 99.5% of 5-HTP | 5 |
| Folic Acid | 100% USP | 28 |
| Vitamin $B_{12}$ | Cyanocobalamin, 100% USP | 5 |

The ingredients are blended with ethanol, water, glycerine, preservative and flavor to provide liquid medication.

Example 5

Composition Containing *Griffonia Simplicifolia*

| Ingredient | Form | Wt % |
|---|---|---|
| Griffonia Simplicifolia | White powder, 99.5% of 5-HTP | 25 |
| Folic Acid | 100% USP | 28 |
| Thiaminic | USP 100% | 20 |
| Vitamin C | USP 100% | 22 |
| Vitamin $B_{12}$ | Cyanocobalamin, 100% USP | 5 |

The above ingredients are blended with cellulose, gelatin, and magnesium stearate to form tablets. The tablets are then coated with food glaze to provide the appropriate daily recommendation.

Example 6

Composition Containing *Hypericum perforatum* Extract

| Ingredient | Form | Wt % |
|---|---|---|
| *Hypericum perforatum* | Dry extract of flower tops with 0.3% hypericin | 70 |
| Vitamin $B_6$ | 100% USP | 10 |
| Folic Acid | 100% USP | 10 |
| Vitamin $B_{12}$ | Cyanocobalamin, 100% USP | 10 |

The ingredients are blended with methylcellulose, stearic acid, cellulose, magnesium stearate, propylene glycol and hydroxypropyl cellulose to produce tablets.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising *Hypericum perforatum* extract and 5-HTP.

2. The composition of claim 1, wherein said composition further comprises a vitamin.

3. The composition of claim 2, wherein said vitamin is selected from the group consisting of thiamine, riboflavin, niacin, folic acid, vitamin C, pantothenic acid, vitamin $B_6$, and vitamin $B_{12}$.

4. The composition of claim 2, wherein said vitamin comprises from about 0.01 percent to about 90 percent of said composition.

5. The composition of claim 2, wherein said vitamin is naturally derived.

6. The composition of claim 2, wherein said vitamin is synthetically derived.

7. The composition of claim 1, wherein said *Hypericum perforatum* extract comprises a dry extract or a concentrated extract of *Hypericum perforatum* flower tops or leaves.

8. The composition of claim 1, wherein said *Hypericum perforatum* extract comprises up to about 90 percent of said composition.

9. The composition of claim 1, wherein said 5-HTP comprises up to about 90 percent of said composition.

10. The composition of claim 1, wherein said composition is in the form of a tablet, encapsulate, or syrup.

11. The composition of claim 1, wherein said composition is in the form of a tablet, and said composition comprises a filler, binder, excipient, or coating.

12. The composition of claim 1, wherein said composition is in the form of an encapsulate, and said composition comprises a filler.

13. The composition of claim 1, wherein said composition is in the form of a syrup, and said composition comprises a liquid carrier, preservative, or flavoring.

14. The composition of claim 13, wherein said liquid carrier is selected from the group consisting of ethanol, water, and glycerine.

15. The composition of claim 1, wherein said composition further comprises hypericin, said hypericin comprising from about 0.001 percent to about 5.0 percent of said composition.

16. The composition of claim 1, wherein said composition further comprises quercetin, said quercetin comprising from about 0.001 percent to about 5.0 percent of said composition.

17. The composition of claim 1, wherein said composition further comprises pseudohypericin, said pseudohypericin comprising from about 0.001 percent to about 5.0 percent of said composition.

18. The composition of claim 1, wherein said composition further comprises rutin, said rutin comprising from about 0.001 percent to about 5.0 percent of said composition.

19. The composition of claim 1, wherein said composition further comprises hyperoside, said hyperoside comprising from about 0.001 percent to about 10 percent of said composition.

20. The composition of claim 1, wherein said composition further comprises isoquercetin, said isoquercetin comprising from about 0.001 percent to about 10 percent of said composition.

21. The composition of claim 1, wherein said composition further comprises a hydrophilic phytochemical.

22. The composition of claim 1, wherein said composition further comprises a mineral.

23. The composition of claim 22, wherein said mineral is selected from the group consisting of calcium, magnesium, and chromium.

24. The composition of claim 22, wherein said mineral comprises up to about 25 percent of said composition.

25. The composition of claim 1, wherein said composition further comprises a lipophilic component of a phytochemical.

26. The composition of claim 1, wherein said 5-HTP comprises an extract from *Griffonia simplicifolia, Mucana pruriens* of legume, *Musa sapientum, Gossypium hirsutum,* or *Urtica dioica*.

27. The composition of claim 1, wherein said 5-HTP comprises more than about 0.01 percent of said composition.

28. The composition of claim 1, wherein said 5-HTP comprises optically pure L-configuration 5-HTP.

29. The composition of claim 1, wherein said composition further comprises a *Ginko biloba* extract.

30. The composition of claim 1, wherein said composition further comprises a *Piper methysticum* extract.

* * * * *